(12) United States Patent
Moore

(10) Patent No.: US 11,246,759 B1
(45) Date of Patent: Feb. 15, 2022

(54) ADHESIVE BANDAGE SYSTEM AND METHOD OF USE

(71) Applicant: Niels Moore, Dedham, MA (US)

(72) Inventor: Niels Moore, Dedham, MA (US)

(*) Notice: Subject to any disclaimer, the term of this patent is extended or adjusted under 35 U.S.C. 154(b) by 6 days.

(21) Appl. No.: 17/066,531

(22) Filed: Oct. 9, 2020

Related U.S. Application Data

(60) Provisional application No. 62/940,479, filed on Nov. 26, 2019.

(51) Int. Cl.
*A61F 13/00* (2006.01)
*A61F 13/02* (2006.01)

(52) U.S. Cl.
CPC ...... *A61F 13/0008* (2013.01); *A61F 13/0266* (2013.01); *A61F 2013/00812* (2013.01)

(58) Field of Classification Search
CPC .. A61F 2013/00817; A61F 2013/00089; A61F 13/00; A61F 13/0008; A61F 13/00812; A61F 13/00089; A61F 13/00021; A61F 13/00072; A61F 13/00076; A61F 13/00085; A61F 13/02; A61F 13/0259; A61F 13/0266; A61F 13/60; A61F 15/001; A61F 13/069; A61F 13/14; A61F 13/06; A61F 13/061; A61F 13/063; A61F 13/064
USPC ........... 602/41–43, 52, 54, 57–60, 900, 904; 128/888–894; 206/440–441; 604/304; 424/443, 445–446
See application file for complete search history.

(56) References Cited

U.S. PATENT DOCUMENTS

| | | | | |
|---|---|---|---|---|
| 6,297,422 B1* | 10/2001 | Hansen | ........... | A61F 13/023 602/54 |
| 7,129,389 B1* | 10/2006 | Watson | ........... | A61F 13/0276 602/48 |
| 2005/0256439 A1* | 11/2005 | Grossman | ........... | A61F 15/002 602/57 |
| 2007/0173752 A1* | 7/2007 | Schonfeldt | ........... | A61F 13/0259 602/57 |
| 2012/0292426 A1* | 11/2012 | Arefieg | ........... | B26D 3/02 242/590 |
| 2013/0289465 A1* | 10/2013 | Hohnbaum | ........... | A61F 13/024 602/57 |
| 2014/0116907 A1* | 5/2014 | Holstein | ........... | A61F 13/0008 206/441 |
| 2015/0320605 A1* | 11/2015 | Pigg | ........... | A61F 13/15707 604/385.05 |

* cited by examiner

*Primary Examiner* — Caitlin A Carreiro
(74) *Attorney, Agent, or Firm* — Leavitt Eldredge Law Firm

(57) ABSTRACT

An adhesive bandage system includes a bottom package strip; a top package strip secured to the bottom package strip at a first end tab; a bandage, the bandage having a body and an adhesive layer and gauze, the adhesive layer removably engaged with an interior surface of the bottom package strip; and an applicator tab attached to a first end of the body of the bandage, the applicator tab extending outside of the bottom package strip and the top package strip; wherein the bandage is removed from between the bottom package strip and the top package strip via pulling force applied to the applicator tab.

3 Claims, 5 Drawing Sheets

ADHESIVE BANDAGE SYSTEM AND METHOD OF USE

BACKGROUND

1. Field of the Invention

The present invention relates generally to bandage systems, and more specifically, to a bandage system that utilizes an applicator tab, thereby preventing the user from coming into contact with the adhesive and allowing for easy application of the bandage.

2. Description of Related Art

Bandage systems are well known in the art and are effective means to help protect and heal a minor wound. For example, FIG. 1 depicts a conventional bandage 101, having a bandage body 103 configured to secure to a user's skin. In FIG. 2, a flowchart 201 depicts the conventional use of bandage 101. During use, the bandage is conventionally stored between a top and bottom of a package, the bandage having an adhesive cover further covering the adhesive bottom, as shown with box 203. The user will peel apart the top and bottom, thereby allowing for removal of the bandage, as shown with box 205. The user will then have to remove the adhesive cover to reveal the adhesive and apply the bandage, as shown with boxes 207, 209.

One of the problems commonly associated with bandage 101 is inconvenience. For example, the user may have a tough time getting the bandage free from the packaging and adhesive covering without contaminating the bandage, or the like. This can lead to wasted bandages and/or unsanitary conditions.

Accordingly, although great strides have been made in the area of bandage systems, many shortcomings remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
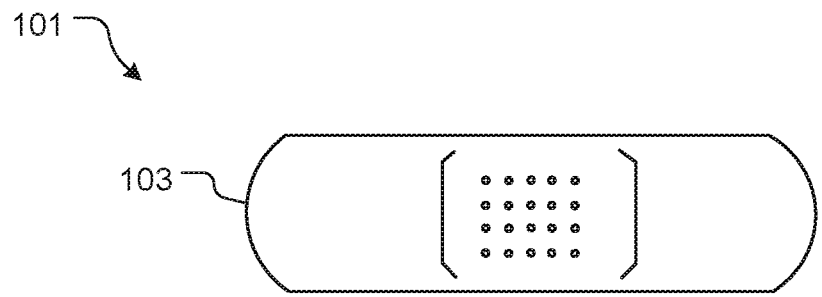
FIG. 1 is a top view of a common bandage system.
Figure 2:
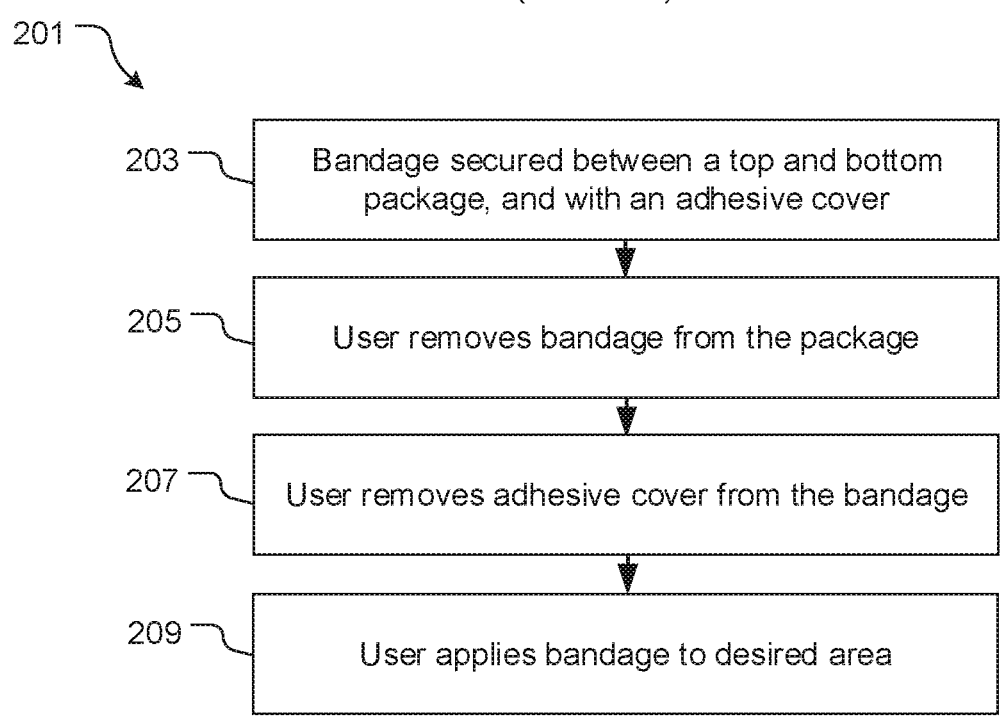
FIG. 2 is a flowchart of a method of use of a conventional bandage system.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional bandage systems. Specifically, the present invention provides for use of an applicator tab, wherein the user can utilize the applicator tab to remove the bandage from its adhesive cover and apply the bandage, thereby preventing the user from coming into contact with the bandage adhesive and gauze. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Figure 3:
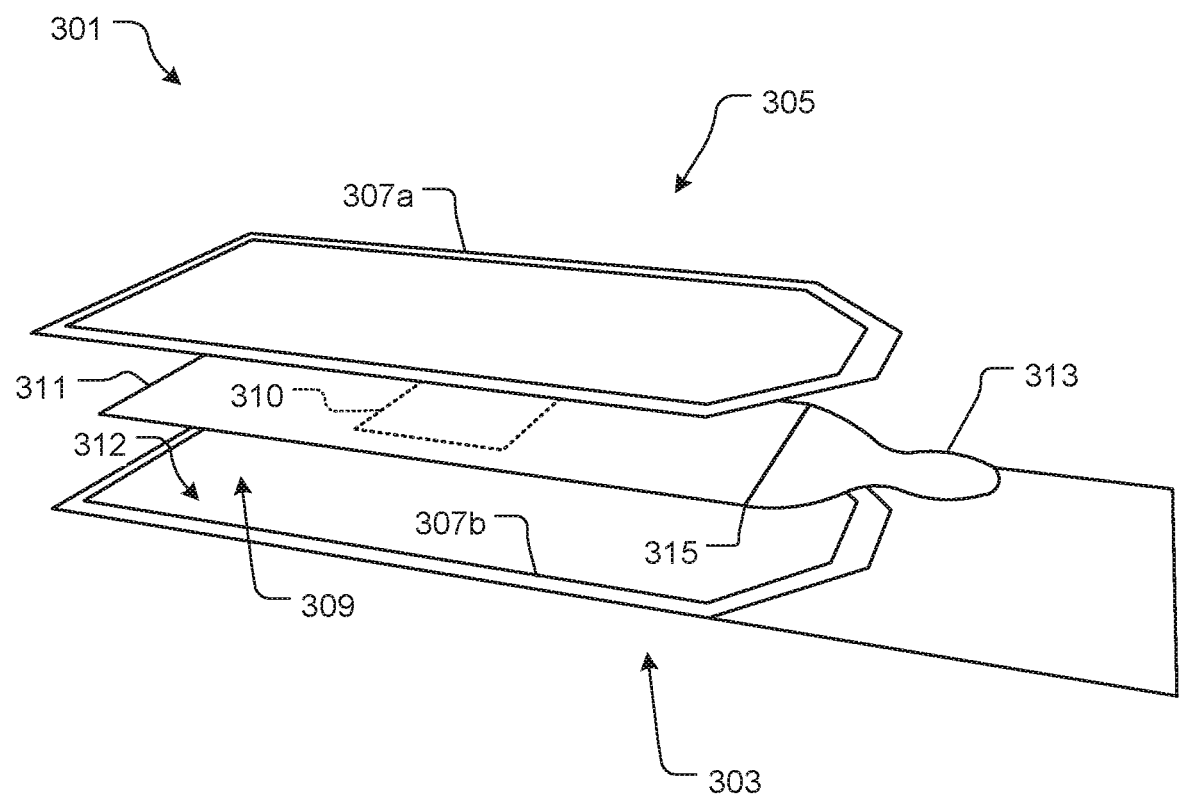
FIG. 3 is an isometric view of a bandage system in accordance with a preferred embodiment of the present application.

Referring now to the drawings wherein like reference characters identify corresponding or similar elements throughout the several views, FIG. 3 depicts an isometric exploded view of an adhesive bandage system 301 in accordance with a preferred embodiment of the present application. It will be appreciated that system 301 overcomes one or more of the above-listed problems commonly associated with conventional bandage systems.

In the contemplated embodiment, system 301 includes a bottom package strip 303 and a top package strip 305 configured to secure to the bottom package strip via an adhesive seal 307a, 307b. As shown, the adhesive seal is configured to extend around the entire periphery of the top package strip 305, thereby providing for a sanitary enclosure, wherein a bandage 309 is secured.

In the preferred embodiment, the bandage 309 includes a body 311 and an adhesive layer 401, the adhesive layer 401 removably engaged with an interior surface 312 of the bottom package strip. As will be discussed more in connection with FIGS. 4 and 5.

It should be appreciated that the bandage 309 can vary, and can include a gauze pad 310, antibacterial ointments (not shown), or other features.

As shown, system 301 further includes an applicator tab 313 attached to a first end 315 of the body of the bandage, the applicator tab extending outside of the adhesive seal of the bottom package strip and the top package strip when secured together. It should be appreciated that the bandage 309 is configured to be positioned between the top package strip and the bottom package strip, within the sanitary enclosure. The tab 313 will extend therefrom and provide for a gripping location to provide removal of the bandage from the top and bottom packaging.

It should be appreciated that one of the unique features believed characteristic of the present application is the configuration of the system with the applicator tab, the applicator tab providing a means to remove the bandage from its protective packaging, and further to apply the bandage to the desired location, all while creating an environment wherein the user does not have to touch the bandage adhesive or gauze and break sanitation.

Figure 4A:
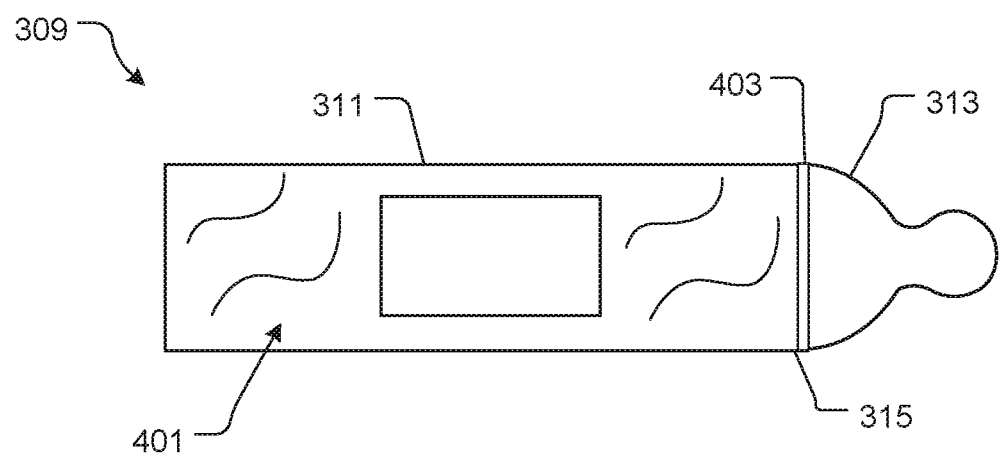
FIGS. 4A and 4B are bottom views of the bandage and applicator tab of FIG. 3.
Figure 4B:
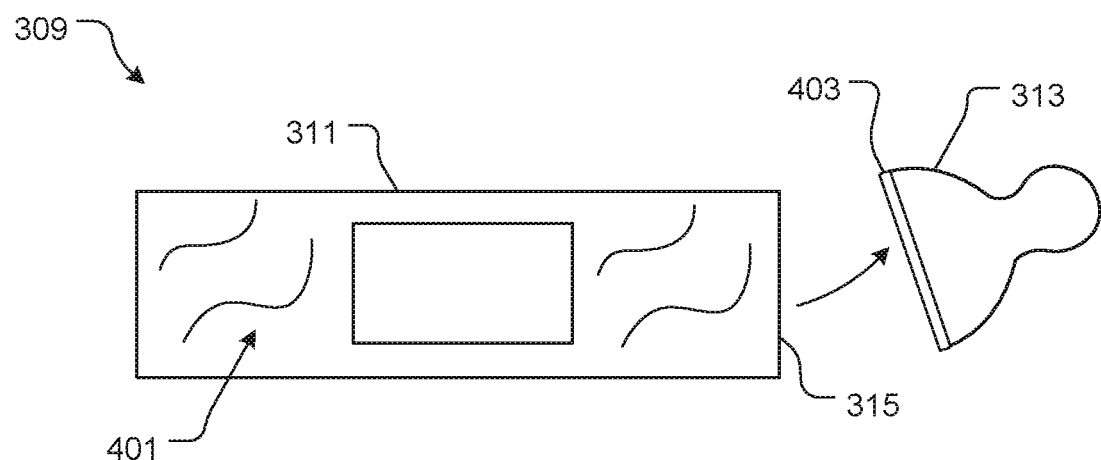

In FIGS. 4A and 4B, bottom views of bandage 309 is shown, wherein the applicator tab 313 is attached to body 311 at first end 315. As shown, the applicator tab 313 is attached via a tear away connection 403. This allows for the user to easily remove the applicator tab 313 from the body 311 once applied to the desired location. As shown, the bandage 309 includes adhesive layer 401 that allows for application to the user's skin.

Figure 5:
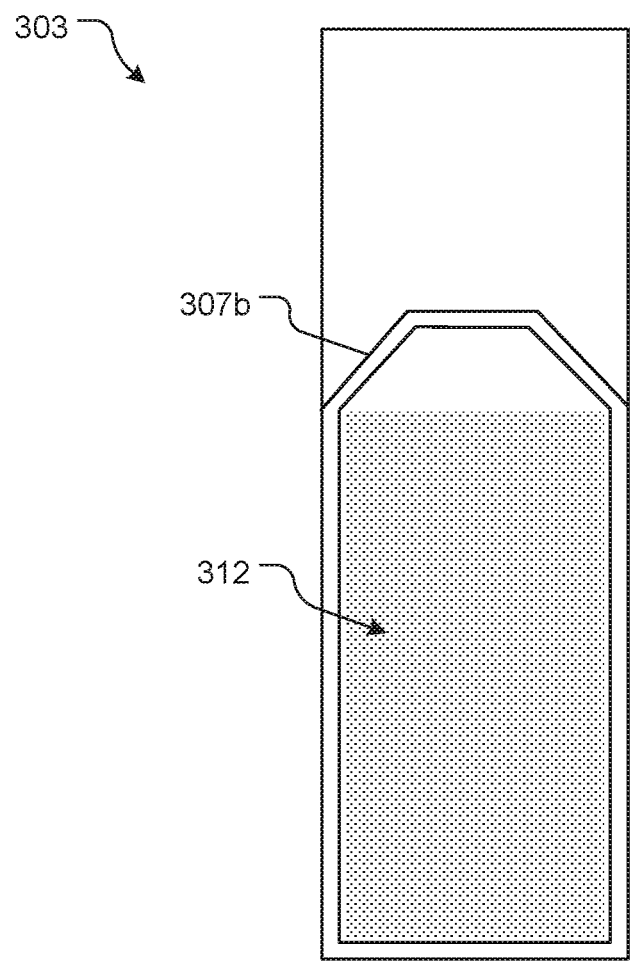
FIG. 5 is a top view of the bottom package strip of FIG. 3.

In FIG. 5, a top view of bottom package strip 303 is shown. As shown, the interior layer 312 includes an adhesive cover, the adhesive cover configured to removably secure to the adhesive layer of the bandage. It should be appreciated that the adhesive layer will remove easily from the cover. This feature prevents the user from having to remove the adhesive cover with their hands, which could potentially result in contaminating the bandage.

Figure 6:
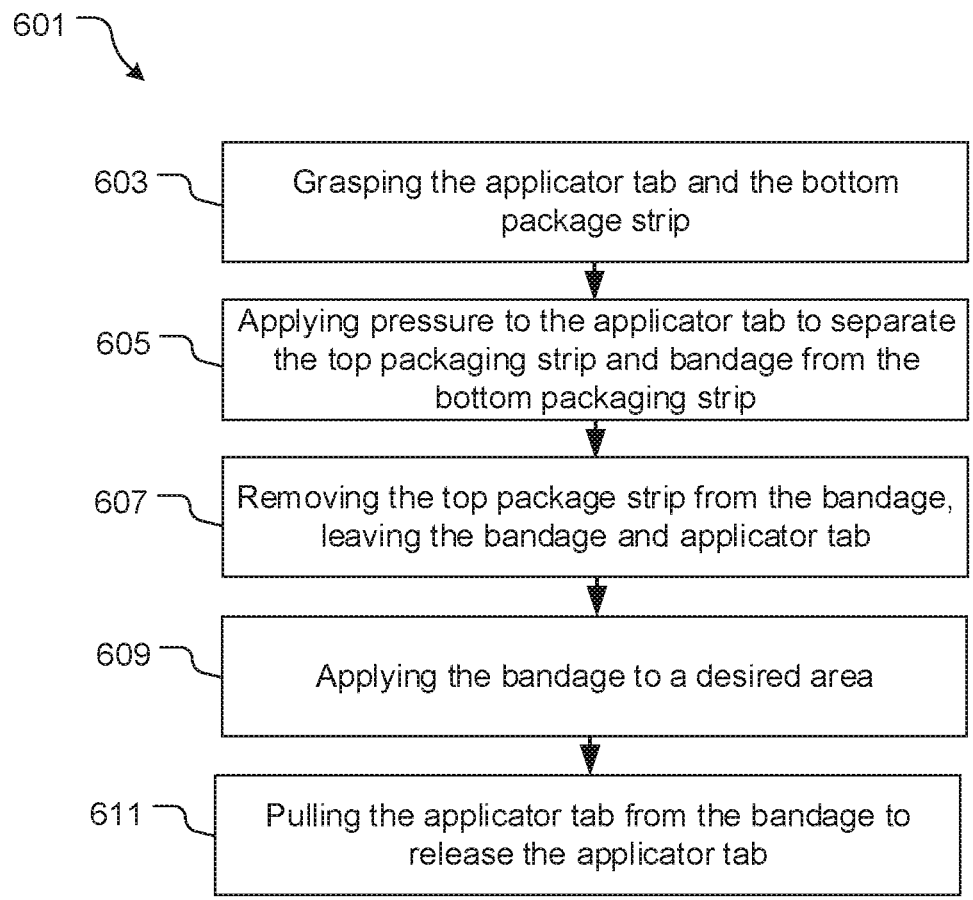
FIG. 6 is a flowchart of a method of use of the system of FIG. 3.

In FIG. 6, a flowchart 601 depicts the method of use of system 301. During use, the user will grasp the applicator tab, such as between their index finger and thumb, as shown with box 603. The user will simultaneously grasp bottom package strip 303 by the end adjacent to applicator tab 313, such as between their opposite index finger and thumb, as shown with box 603. The user will then apply a pulling force to the tab, peeling the bandage and top packaging strip away from the bottom packaging strip, as shown with box 605. The user will continue to hold the applicator tab and pull the top packaging strip away, as shown with box 607. The user will then use minimal contact with the bandage to apply the bandage to a desired location, as shown with box 609. Once the bandage is in place, the user can pull off the applicator tab, as shown with box 611.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. An adhesive bandage system, comprising:
   a bottom package strip being rectangular and having a first end, a second end opposite the first end, and an inner surface;
   a top package strip having a first end and a second end opposite the first end, wherein the first end of the top package strip has a shape defined by a side edge that extends perpendicularly between upper and lower edges that are parallel to one another and wherein the second end of the top package strip is configured to have a trapezoid shape, wherein the top package strip is secured to the bottom package; strip by an adhesive seal, the adhesive seal positioned around an entire periphery edge of the top package strip, wherein the first end of the bottom package strip is secured to the first end of the top package strip by the adhesive seal and the second end of the bottom package strip extends beyond the second end of the top package strip and beyond the adhesive seal;
   a bandage having a body with a top surface, a gauze pad, and an adhesive layer that is configured to allow for application of the bandage to skin of a user, wherein the adhesive layer and gauze pad are both secured to the top surface of the body of the bandage, wherein the adhesive layer is removably engaged with an adhesive cover on the inner surface of the bottom package strip;
   an applicator tab configured as a protrusion extending away from the bandage and having a rounded terminal end, the applicator tab attached to a first end of the body of the bandage, wherein the applicator tab extends beyond the adhesive seal to a position outside of the adhesive seal, wherein the rounded terminal end of the applicator tab is positioned at a location that is between the adhesive seal and the second end of the bottom package strip such that the applicator tab does not extend past the second end of the bottom package strip;
   a tear away connection between the first end of the body of the bandage and the applicator tab;
   wherein the applicator tab is removably attached to the bandage via the tear away connection; and
   wherein the bandage is configured to be removed from between the bottom package strip and the top package strip by a pulling force applied to the applicator tab and bottom package strip.

2. The adhesive bandage system of claim 1, wherein the adhesive seal is configured to create a sterile environment.

3. A method of applying a bandage, the method comprising:
   providing the adhesive bandage system of claim 1;
   grasping the applicator tab; grasping the bottom package strip;
   applying pulling pressure to the applicator tab to separate the bandage and top package strip from the bottom package strip;
   removing the top package strip and the bandage from the bottom package strip;
   removing the bandage from the top package strip via the applicator tab; applying the bandage to a desired area; and
   removing the applicator tab from the bandage.

* * * * *